United States Patent [19]
Heidsieck

[11] Patent Number: 5,218,625
[45] Date of Patent: Jun. 8, 1993

[54] METHOD FOR THE AUTOMATIC DETERMINATION OF THE EXPOSURE TIME OF A RADIOGRAPHIC FILM AND SYSTEM OF IMPLEMENTATION THEREOF

[75] Inventor: Robert Heidsieck, Versailles, France

[73] Assignee: General Electric CGR S.A., Issy les Moulineaux, France

[21] Appl. No.: 726,205

[22] Filed: Jul. 5, 1991

[30] Foreign Application Priority Data

Jul. 6, 1990 [FR] France ................................ 90 08625
Jul. 6, 1990 [FR] France ................................ 90 08628

[51] Int. Cl.$^5$ ............................................. H05G 1/42
[52] U.S. Cl. .................................... 378/97; 378/95; 378/108; 378/207
[58] Field of Search ...................... 378/91, 95–97, 378/99, 108, 207

[56] References Cited

U.S. PATENT DOCUMENTS

| | | | |
|---|---|---|---|
| 3,792,267 | 2/1974 | Westerkowsky | 378/97 |
| 3,894,235 | 7/1975 | Franke | 378/97 |
| 3,974,385 | 8/1976 | Grim | 378/97 |
| 4,178,508 | 12/1979 | Hotta et al. | 378/97 |
| 4,250,103 | 2/1981 | Vatne et al. | 378/97 |
| 4,748,648 | 5/1988 | Boucle et al. | 378/96 |
| 4,763,343 | 8/1988 | Yanaki | |
| 4,811,374 | 3/1989 | Kasa et al. | 378/96 |
| 4,831,642 | 5/1989 | Chattin | 378/97 |

FOREIGN PATENT DOCUMENTS

| | | |
|---|---|---|
| 3641992 | 6/1988 | Fed. Rep. of Germany . |
| 2004437 | 3/1979 | United Kingdom . |
| 8701555 | 3/1987 | World Int. Prop. O. . |

Primary Examiner—David P. Porta
Attorney, Agent, or Firm—Pollock, VandeSande & Priddy

[57] ABSTRACT

The disclosure concerns radiology instruments that include an X-ray source, a receiver of the film or film-screen type, a detection cell and means to compute the yield at the cell. The method consists of performing measurements of the yield at instants $t_1, t_2, \ldots t_3$ during the exposure, so as to determine the lumination or luminous exposure (the quantity of the light received multiplied by the exposure time) on the film and then computing the lumination remaining to be acquired to obtain the chosen optical density on the film.

33 Claims, 4 Drawing Sheets

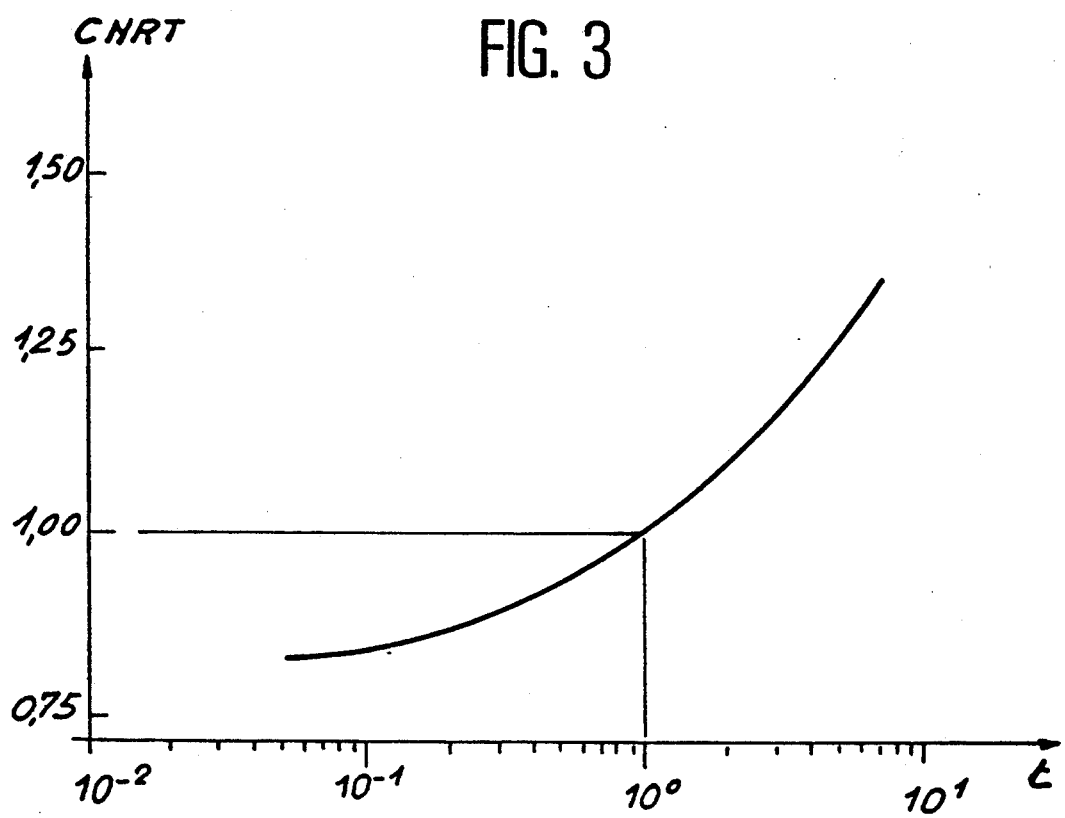
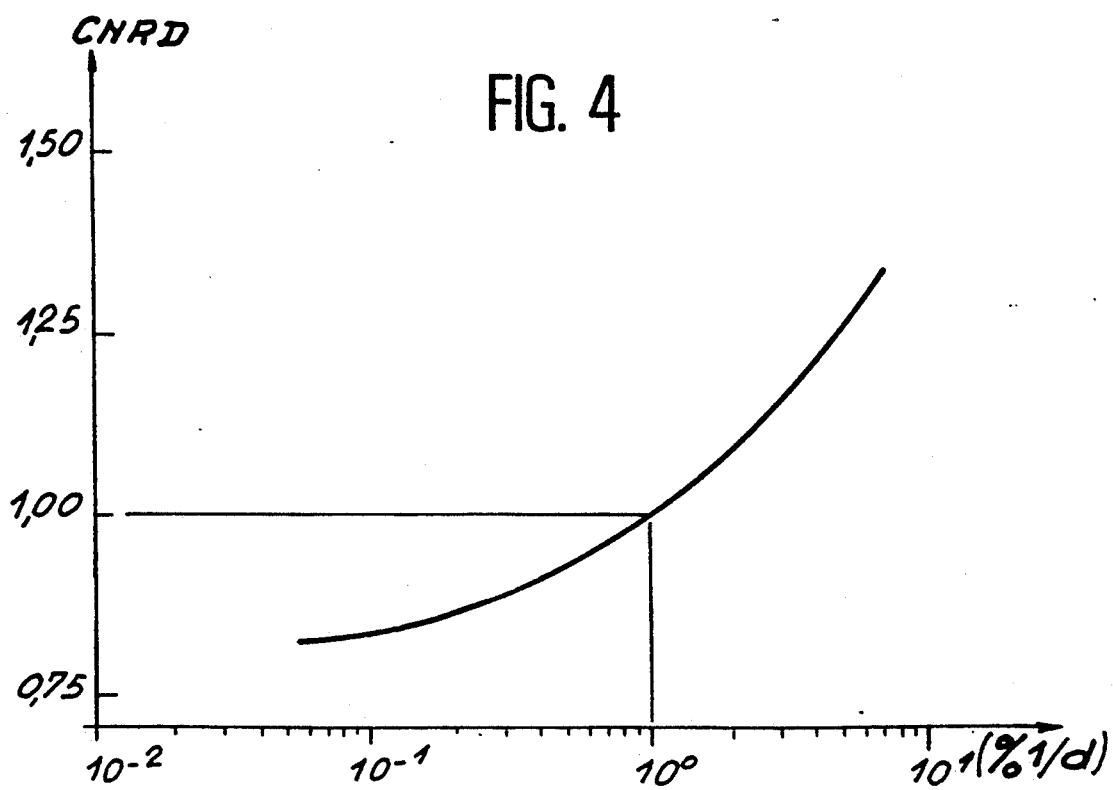

METHOD FOR THE AUTOMATIC DETERMINATION OF THE EXPOSURE TIME OF A RADIOGRAPHIC FILM AND SYSTEM OF IMPLEMENTATION THEREOF

BACKGROUND OF THE INVENTION

1. Field of the Invention

The invention relates to radiology systems that have a radiological film and are used to examine objects and, more particularly in such systems, it relates to a method that enables the estimation, while the object is being examined, of the "lumination" or "luminous exposure" (i.e. the quantity of light received multiplied by the exposure time) to which the radiological film is subjected, and enables the stopping of the exposure when the film has reached a given level of blackening or optical density.

2. Description of the Prior Art

A radiology system essentially comprises an X-ray tube and a receiver of such radiation, between which the object to be examined, for example a part of a patient's body, is interposed. The image receiver which is, for example, a film/screen couple, gives an image of the object after an appropriate exposure time and the development of the film. For the image of the object to be used as efficiently as possible, the different dots that constitute it should have sufficient contrast with respect to one another, namely, the blackening of the radiographic film should be appropriate from one X-ray image to the next one, despite the possible differences in opacity of the radiographed object.

The blackening of the film is related to the quantity of energy of the radiation incident to the film/screen couple, namely, the product of the intensity of the radiation to which the radiographic film is subjected, or "film" dose rate, by the time during which the film is exposed to this radiation. Consequently, to obtain a constant blackening of the film from one radiography to another, there is a known way of making measurements, during the examination, of the incident energy on the film by means of a detection cell, generally placed before the receiver, that is sensitive to X-radiation and gives a current proportional to the "film" dose rate. This current is integrated, from the start of the exposure, in an integrator circuit that gives an increasing value during the exposure. This increasing value is compared, during the exposure time, with a fixed reference value, established beforehand as a function of the characteristics of the film. The end of the exposure time is determined by the instant at which the comparison indicates that the value representing the incident energy on the film is equal to the reference value.

Should the radiographic film be directly subjected to X-radiation, and should the variation in the exposure times from one examination to another be small enough, a constant blackening of the film is obtained from one exposure to the next one, independently of the duration of the exposure time S, provided that the product of the exposure time S by the dose rate F is constant, i.e. the value resulting from the integration should remain constant.

This is true only if the characteristics of the film obey the law of reciprocity which indicates that the optical density of the film is proportional to the product $F \times S$ and if the response of the film is independent of the quality of the incident X-ray beam.

This law of reciprocity is no longer met when the variation in the exposure times is great.

Besides, should the radiographic film be associated with an intensifying screen, the blackening of the film depends on the quality of the spectrum. For, the response of the screen depends on the energy distribution of the spectrum of the radiation received, which means that it is sensitive to the hardening of the spectrum and to the change in voltage of the X-ray tube.

Finally, there are certain applications wherein it is costly for the detection cell to be placed before the film (for example in mammography) for the radiation energy is such that the detection cell would then be visible on the film. In this case, it is placed behind the image receiver but this creates an additional difficulty for the signal perceived by the detector cell is the one that has not contributed to the blackening of the film. The result thereof is that the measurement made by the detection cell does not generally represent the incident lumination on the radiographic film.

The deviation from the law of reciprocity, which varies according to the type of film, represents the relative variation of the lumination needed to obtain a constant optical density when the exposure time S varies while the spectrum of the X-radiation is constant. This is expressed by the fact that, to obtain a same optical density of the film, the lumination should be, for example 1 for an exposure time $S = 0.1$ second, 1.3 for $S = 1$ second and 2 for $S = 4$ seconds.

This deviation from the law of reciprocity is due to the phenomenon known as the Schwarzschild effect. This effect is described notably in the work by Pierre GLAFKIDES, *CHIMIE ET PHYSIQUE PHOTOGRAPHIQUES*, 4th edition, pages 234 to 238, PUBLICATIONS PHOTO-CINEMA Paul MONTEL.

To account for this deviation from the law of reciprocity, various approaches have been proposed, and one of them has been described in the French patent No. 2 584 504. This patent proposes the comparison of the integrated value of the signal given by the detection cell with a reference value that varies during the exposure according to a determined relationship. More precisely, from the start of each exposure period, an additional value is added to the difference between the values of the integrated signal and of the reference value. This additional value increases as a function of time according to a previously determined relationship, for example an exponential relationship.

This previously determined relationship, whether it is exponential or otherwise, takes account of the deviation from the law of reciprocity only imperfectly. In particular, it does not take account of the variations in the luminous intensity effectively received by the film.

Furthermore, this correction does not take account of the effects of other phenomena such as the hardening of the X-radiation due to the thickness of the object crossed and the modification of the spectrum due to the voltage of the X-ray tube.

Furthermore, in this method, the detection cell is placed before the image receiver.

An object of the present invention, therefore, is to implement a method for the automatic determination, during the time of exposure, of the instant when the exposure is stopped, taking account of the different effects that come into play, notably the variations in the tube current, the hardening of the spectrum due to the thickness of the object crossed, the modification of the spectrum due to the voltage of the tube and, when an intensifier screen is present, the absorption response of said screen.

SUMMARY OF THE INVENTION

The invention relates to a method for automatically determining the exposure time of a radiographic film in a radiology system designed, to examine an object that includes an X-ray tube having a supply voltage V which may assume various values, $V_m$, with continuous or discrete variation. The X-ray tube emits an X-ray beam in the form of pulses of variable duration S towards the object to be examined. A receiver detects the X-radiation that has crossed the object, to form an image of said object. The receiver is constituted by at least one intensifier screen and a film sensitive to the light emitted by this screen. A cell detects the X-rays that have crossed the object, to be examined and is placed behind the image receiver to enable the conversion of a physical variable, characterizing the X-ray beam, into a measurement signal L. An integrator circuit integrates the measurement signal L for, the duration S of the exposure and produces a signal M a device computes the yield D given by determining the ratio of M to the product $I \times S$ (or mA·s) of the anode current I of the tube by the duration S of the exposure. The method includes the following operations.

(a) A first calibration of the radiology system by means of objects with a thickness $E_p$ by using a receiver without the intensifier screen or screens so as to determine the function:

$$D_{se} = f'(V_m, E_p) \qquad (4)$$

and the inverse function:

$$E_p = g'(V_m, D_{se}) \qquad (5)$$

(b) A second calibration of the radiology system by means of the objects with a thickness $E_p$ by using a receiver with intensifier screen so as to determine the function:

$$D_c = f''(V_m, E_p) \qquad (6)$$

the inverse function $$E_p = g''(V_m, D_c) \qquad (7)$$

and the function $$D_f = f'(V_m, E_p) - f''(V_m, E_p) \qquad (8)$$

(c) A third calibration to determine the reference lumination $L_{ref}$ that must be received by the film, under fixed reference conditions, to achieve the blackening (or optical density) chosen as a reference value by the practitioner.

When these calibration operations have been performed, it is possible to go on to the radiological examination of the object which consists of the following steps of (or operations for) :

(e1) positioning the object to be radiographed;
(e2) triggering the start of the exposure by the practitioner;
(e3) measuring the yield $D_{c1}$ at a certain time t' after the start of the exposure;
(e4) calculating the equivalent thickness $E_1$ by the equation (7);

(e5) calculating the yield $D_{f1}$ at the film for the thickness $E_1$ by the equation (8);
(e6) calculating the lumination $L_f$ received by the film according to the equation:

$$L_f = L_{am} + D_{f1} \times \delta mA \cdot s \qquad (9)$$

(e7) calculating the lumination $L_{ra}$ remaining to be acquired to obtain the blackening (or optical density) chosen by the equation:

$$L_{ra} = L_{ref} - L_f \qquad (10)$$

(e8) calculating the estimated mA·s remaining to be delivered $mAs_r$ to obtain the blackening (or optical density) chosen by the equation :

$$mAs_r = L_{ra}/D_{f1} \qquad (11)$$

(e9) measuring the mA·s delivered $mAs_{mes}$ from the start of the operation (e3);
(e10) stopping the exposure when the mA·s measured $mAs_{mes}$ (in e9) are equal to or greater than $mAs_r$, —or returning to the step (e3) when the mA·s measured (in e9) are smaller than $mAs_r$.

To take account of the time $t_o$ of the operations (e4) to (e8), the step (e8) further includes the calculating of the mA·s delivered ($mAs_c$) during the steps (e4) to (e8) defined by the equation:

$$mAs_c = I \times t_c \qquad (13)$$

which makes it possible to determine the real value of the mA·s remaining to be acquired ($mAs_{ra}$) by the equation:

$$mAs_{ra} = mAs_r - mAs_c \qquad (12)$$

In a first variant, the step (e10) further includes a step of computing the remaining exposure time, such that $$t_{rc} = \frac{mAs_{ra}}{I} \qquad (14)$$

so as to end the exposure in an open loop if $t_{rc}$ is smaller than a value t" corresponding to the interval of time between two successive operations (e3).

In a second variant, the steps (e3) to (e10) are replaced by:

a task of estimation (T.E.) of the mA·s remaining to be delivered, constituted by the steps (e4) to (e8) and a step of converting the mA·s into a signal in the units of the cell 12 such that:

$$CE_{target} = mAs_{ra} \times D_c \qquad (16)$$

a task of interrupting (T.C.) the exposure which consists in decrementing the target value $CE_{target}$ by the signals received by the cell (12) and in terminating the exposure when the decremented value becomes smaller than or equal to a value $Val_o$ ($Val_o$ is equal to zero for example).

The task of estimation (T.E.) is renewed periodically during the exposure at the instants $t_1, t_2, \ldots t_n$ separated by a period that is at least equal to the computation time $t_c$.

In another variant, the step (e10) is replaced by the step of computing the remaining exposure time $t_{rc}$ so as to end the exposure in an open loop.

To take account of the effect of non-reciprocity of the film, the steps (e6) and (e8) are modified to introduce a coefficient CNRD (film dose rate) of non-reciprocity of the film into the equations (9) and (11) which become:

$$L_f = L_{am} + D_{fl} \times \delta mA \cdot s/CNRD \text{ (film dose rate)} \quad (9')$$

and $$mAs_{ra} = \frac{L_{ra}}{D_{fl}} \times CNRD \text{ (film dose rate)} \quad (11')$$

These are formulae in which CNRD (film dose rate) is the coefficient of non-reciprocity indexed as a function of the film dose rate of the receiver such that:

$$\text{film dose rate} = D_{fl} \times I \quad (17)$$

The coefficient CNRD (film dose rate) is obtained by performing the following steps of:

measuring the coefficients of non-reciprocity CNRT $(t_i)$ of the film/screen couple as a function of the exposure time $(t_i)$, measuring for each exposure time $(t_i)$ the film dose rate $d_i$, determining the function of modelization of the coefficients CNRD $(d_i)$ such that:

$$CNRD\ (d) = A'_0 + A'_1 \log 1/d + A'_2 [\log 1/d]^2 \quad (20)$$

which makes it possible to determine the coefficient corresponding to a given film dose rate.

The film dose rate $d_i$ is given, for example, by the formula:

$$d_i = \frac{L_{ref} \times CNRT(t_i)}{t_i} \quad (22)$$

The reference lumination $L_{ref}$ is determined by a calibration method that includes the following steps of (or operations for):

taking a shot under determined radiological conditions for a reference optical density $DO_{refo}$, a thickness standard $E_o$, a supply voltage $V_o$, an exposure time $t_o$ a value of the product $I_o \times t_o$;

measuring the yield $D_o$;

calculating the equivalent thickness $E_{po}$ by the formula:

$$E_{po} = g''\ (V_o, D_o) \quad (7)$$

calculating the yield $D_{fo}$ on the film by the formula:

$$D_{fo} = f'(V_o, E_o) - f''\ (V_o, E_o) \quad (8)$$

calculating the luminance $L_{film}$ on the film by the formula:

$$L_{film} = \frac{D_{fo} \times I_o \times t_o}{CNRT(t_o)} \quad (23')$$

calculating the illumination step $Ech_{ref}$ corresponding to the reference optical density $DO_{refo}$ by means of the sensitometric curve;

measuring the optical density $DO_m$ of the shot obtained and calculating the illumination step $Ech_m$ by means of the sensitometric curve;

calculating the reference lumination $L_{ref}$ by the formula:

$$L_{ref} = L_{film} \times \exp\left[\log_{10}\left[\frac{Ech_{ref} - Ech_m}{K}\right]\right] \quad (25)$$

with $K = 2/\log_{10}(2)$ \quad (26)

The coefficients of non-reciprocity CNRD(d) as a function of the film dose rate are obtained by r performing the following operations:

measuring the coefficients of non-reciprocity CNRT $(t_i)$ of the film/screen couple as a function of the exposure time $(t_i)$, measuring, for each exposure time $(t_i)$, the film dose rate $d_i$, determining the function of modelization of the coefficients CNRD (di) such that:

$$CNRD\ (d) = A'_0 + A'_1 \log 1/d + A'_2 [\log 1/d]^2 \quad (20)$$

which makes it possible to determine the coefficient corresponding to a given film dose rate.

The coefficients of non-reciprocity CNRT $(t_i)$ as a function of the exposure time $(t_i)$ may be obtained in different ways, for example by performing the following steps of:

(a1) modifying the tube heating current so as to obtain different values of said current, (a2) reading the values $M(t_i)$ given by the integrator circuit for different exposure times so as to obtain an optical density $DO_1$ of the film (a3) calculating the ratio $$\frac{M(t_i)}{M(t_{ref})} \quad (29)$$

which gives the coefficient CNRT $(t_i)$ with $M(t_{ref})$ the value $M(t_i)$ for $t_i = t_{ref}$ The coefficients CNRT $(t_i)$ may be modelized by the function:

$$CNRT\ (t) = A_0 + A_1 \log t + A_2 [\log t]^2 \quad (18)$$

Should the image receiver of the radiology apparatus be of the film type, in which the detection cell is placed before or after the image receiver, the operations (a),(b),(c), and steps (e1) to (e10) described here above are reduced to the following steps of:

(a') calibrating the radiology system so as to determine the analytical model:

$$D'_f = f'''\ (V_m, E_p) \quad (30)$$

(c') with the film as an image receiver, determining by calibration the reference lumination $L'_{ref}$ that should be received by the film, under fixed reference conditions, to achieve the blackening (or optical density) chosen as a reference value by the practitioner;

(e'1) positioning the object to be radiographed;

(e'2) triggering the start of the exposure by the practitioner;

(e'3) measuring the yield $D'_{fl}$ a certain time t' after the start of the exposure;

(e'6) calculating the lumination $L'_f$ received by the film by the equation:

$$L'_f = L_{am} + D'_{fl} \times \delta mA \cdot s / CNRD \text{ (film dose rate)} \quad (9'')$$

(e'7) calculating the lumination $L'_{ra}$ remaining to be acquired to obtain the blackening (or optical density) chosen by the equation:

$$L'_{ra} = L'_{ref} - L'_f \quad (10'')$$

(e'8) calculating the estimated mA·s remaining to be delivered $mAs'_{ra}$ to obtain the blackening (or optical density) by the equation:

$$mAs'_{ra} = L'_{ra}/D'_{fl} \times CNRD \text{ (film dose rate)} \quad (11'')$$

the other steps (e9) and (e10) that follow being unchanged.

BRIEF DESCRIPTION OF THE DRAWINGS

Other objects, features and advantages of the present invention shall appear from the following description of the method according to the invention and from a particular exemplary embodiment of the radiology system used to implement it, said description being made with reference to the appended drawings, of which:

FIG. 3 is a graph showing a curve of variation of the coefficients of non-reciprocity CNRT as a function FIG. 4 is a graph showing curves of variation of the coefficients of non-reciprocity CNRD as a function of the inverse of the film dose rate d.

DETAILED DESCRIPTION OF THE INVENTION

Figure 1:
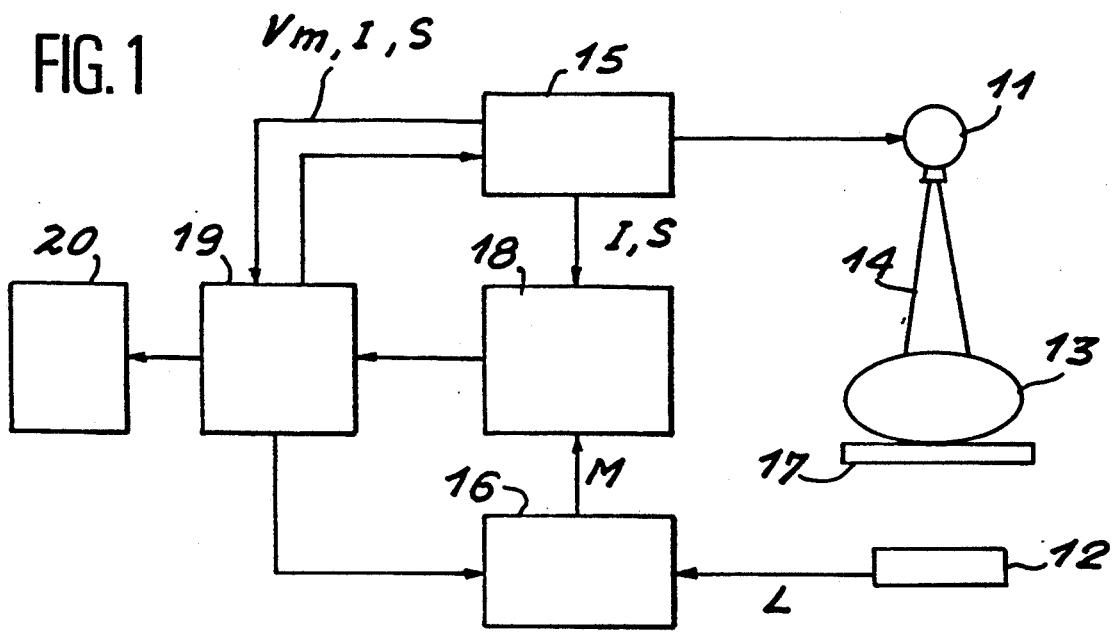
FIG. 1 is a block diagram of a radiology system enabling the implementation of the method according to the invention.

A radiology system to which the method, according to the invention, for the automatic determination of the exposure time of an object 13 to be radiographed, can be applied, comprises an X-ray source 11 such as an X-ray tube that gives an X-ray beam illuminating this object 13 and an image receiver 17 such as a film/intensifier screen couple that is positioned so as receive the X-rays having crossed said object and that gives an image of the object 13 after an appropriate exposure time S and development of the film.

To implement the method of the invention, the system further includes a detection cell 12, that is placed behind the image receiver 17 in the case of a radiographic film with an intensifier screen. This cell may be placed in front of the receiver in the case of a film without an intensifier screen. The detection cell 12 enables the conversion of a physical variable characteristic of the X-radiation that has crossed the object and the image receiver, such as the KERMA or the energy fluence into a measurement signal L, for example of the electrical type. The signal L, produced by the detection cell 12, is applied to a circuit 16 that carries out an integration of the electrical signal during the duration S of the exposure. The signal M that results from the integration is a measurement of the radiation that has crossed the object 13 during the duration S of the exposure.

The X-radiation source 11 is associated with a power supply 15 that produces a variable high voltage $V_m$ for the X-ray tube and includes an instrument for the measurement of the anode current I of said tube. In order to modify the duration of the exposure time S, the power supply device 15 and the X-ray tube include means to start the X-ray emission at a precise instant and to stop it after a variable time S. Time s is determined, in accordance with the invention, as a function of the signal M produced by the circuit 16 and of the values of I, S and $V_m$ and, more precisely, of the ratio $M/I \times S$ which is called the yield D and is computed by the device 18. The values of the yield D are processed by a computer or microprocessor 19 in accordance with the method of the invention so as to give an end-of-exposure signal.

The first operation of the method consists of performing a calibration of the radiology system of FIG. 1 that leads to a function of estimation of the lumination received by the radiographic film. This calibration and the function of estimation are described in the French patent application filed on the same date and entitled: METHOD FOR THE ESTIMATION AND CALIBRATION OF THE LUMINATION RECEIVED BY A RADIOGRAPHIC FILM corresponding to U.S. Pat. application Ser. No. 07/726,204, filed Jul. 5, 1991.

For an understanding of the remaining part of the description, it shall be recalled that the method for estimating the lumination received by a radiographic film is based on calibration operations that result in the definition of a function that is proportional to the dose rate of photons on to the film, called the film dose rate, and on a calibration that can be used to establish the relationship between the film dose rate function and the lumination received by the film under fixed reference conditions and results in a given blackening of the film. This latter calibration shall be described in fuller detail hereinafter in the description.

The calibrations that enable a definition of a film dose rate function are derived from a calibration method described in U.S. patent application Ser. No. 07/535 520 filed on Jun. 8, 1990 and entitled: METHOD FOR THE CALIBRATION OF A RADIOLOGICAL SYSTEM AND FOR THE MEASUREMENT OF THE EQUIVALENT THICKNESS OF AN OBJECT. This method consists of measuring the yield D of the cell for each standard at the chosen supply voltages $V_m$. More precisely, with a first thickness standard $E_1$, a measurement of yield $D_{1m}$ is made for each value $V_m$ constituting a determined set. These values $D_{1m}$ as a function of the voltage $V_m$ may be entered in a graph to obtain the points 21' of FIG. 2. The measurements of yield D are made for another thickness standard $E_2$ and the values $D_{2m}$, corresponding to the points 22' of FIG. 2, are obtained, and the operation continues thus successively to obtain the other series of points 23', 24' and 25' corresponding respectively to the yields $D_{3m}$ $D_{4m}$ and $D_{5m}$ and to the thicknesses $E_3$, $E_4$ and $E_5$.

Figure 2:
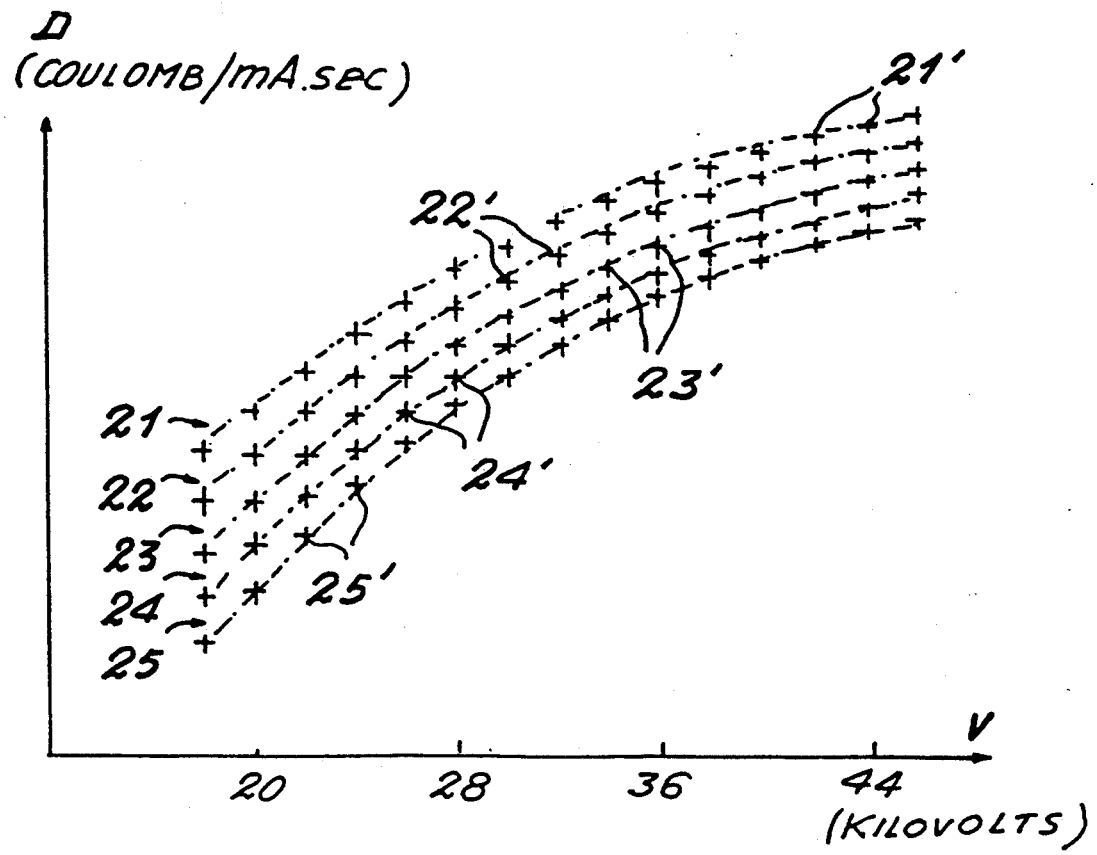
FIG. 2 is a graph showing curves obtained by implementing a method of calibration used in the method according to the invention.

It must be noted that, in FIG. 2, the yields $D_{pm}$ have been entered as logarithmic y-axis values while the supply voltages have been entered as x-axis values from 20 kilovolts to 44 kilovolts.

These series of points 21' to 25' are used to define the parameters of an analytical model that describes the behavior of the yield D as a function of the parameters $V_m$ and $E_p$ for a given configuration of the radiological system. This analytical model shall be written as:

$$D = f(V_m, E_p) \quad (1)$$

The parameters of the analytical model may be adjusted by means of standard estimation tools such as the minimal mean square error method.

The curves 21 to 25 represent the value of the yield D given by the analytical model represented by the expression:

$$D = f(V_m, E_p) = \exp[f_1(V_m) + E_p \times f_2(V_m)] \quad (2)$$

in which $f_1(V_m)$ and $f_2(V_m)$ are second-degree polynomials, the expression of which is given by:

$$f_1(V_m) = A_o + A_1 V_m + A_2 V_m^2$$

$$f_2(V_m) = B_o + B_1 V_m + B_2 V_m^2$$

The inverse function of that expressed by the formula (2) enables $E_p$ to be computed, if D and $V_m$ are known, by using the following formula (3):

$$E_p = g(V_m, D) = \frac{\text{Ln}(D) - f_1(V_m)}{f_2(V_m)} \quad (3)$$

it being known that $f_2(V_m)$ cannot get cancelled for the current values of $V_m$ because the yield D always depends on the thickness $E_p$ at the voltages $V_m$ considered.

In other words, to a couple of values ($E_p$, $V_m$) there corresponds a measurement of yield D, which makes it possible to determine $E_p$ as a function of $V_m$ and D. During a radiological examination, a measurement of yield D, which is done with a given supply voltage $V_m$, makes it possible to determine an equivalent thickness expressed in the units used for $E_p$.

This calibration is performed twice with configurations of the radiology system that differ as regards the receiver 17. The first of these calibration operations is done with the receiver 17 without an intensifier screen. By the equation 1, a function f' is determined, giving rise to yield values of the cell 12 referenced $D_{se}$ such that:

$$D_{se} = f'(V_m, E_p) \quad (4)$$

and the inverse function:

$$E_p = g'(V_m, D_{se}) \quad (5)$$

The second operation of the method consists of performing a second calibration provided with a receiver 17 including an intensifier screen and then a series of yield values $D_c$ is obtained and, as above, the function f" is determined such that:

$$D_c = f''(V_m, E_p) \quad (6)$$

and the inverse function $$E_p = g''(V_m, D_c) \quad (7)$$

From the above two calibration operations, a function $D_f$ is deduced representing the yield on the film such that:

$$D_f = D_{se} - D_c$$

that is $$D_f = f'(V_m, E_p) - f''(V_m, E_p) \quad (8)$$

This function $D_f$ does not take account of the modification of the spectrum of the X-radiation due to the additional filtration between the intensifier screen and the detection cell 12 that comes, for example, from the output face of the cartridge containing the film/screen couple. To take account of it, $E_p$ in the equation (8) is replaced by ($E_p$−sup.filter) where sup.filter is the thickness equivalent to the radiographed object corresponding to this filtration.

This equivalent thickness is obtained by placing, for example, in the beam 14, an object equivalent to this filtration and by using the calibrated function determining the equivalent thickness g' or g" according to the configuration of the machine.

Since the product $D_f \times I \times t$ is proportional to the energy absorbed in the intensifier screen during a duration t and for an anode current I, the quantity $D_f \times I$, referenced film dose rate, is proportional to the dose rate of incident photons on the film and is expressed in the units of measurement of the signal of the detector cell 12. This law of proportionality is verified all the more efficiently as the number of light photons emitted by the intensifier screen is itself proportional to the energy absorbed. If the number of light photons emitted by the screen meets another relationship as a function of the energy absorbed, this other relationship must be applied to $D_f \times I$ to obtain the film dose rate.

A final calibration consists of linking the above-described electrical functions to a value of the blackening of the film, namely to an optical density, that is to be obtained at the end of the exposure. This value is chosen by the practitioner as a function of the film/screen couple, the type of diagnosis, the part of the patient's body to be examined and his usual practices in examining radiographs. This choice makes it possible to determine the reference lumination, referenced $L_{ref}$, namely the lumination that must be received by the film, under fixed reference conditions, to arrive at a degree of blackening such as this. The method used to determine $L_{ref}$ shall be described here below. These calibration operations are not performed at each radiological examination of an object or a patient, but from time to time to take account of the variations in the characteristics of the radiology system in the course of time, notably variations such as the ageing of the X-ray tube. The results of these operations are recorded in the memory of the microprocessor 19 in the form of functions represented by the equations 4 to 8. This means that the microprocessor 19 is capable of computing $E_p$ if it knows $D_c$ and can then compute $D_f$.

During the radiological examination of the patient, the method according to the invention further consists of the performance of the following main steps of (or operations for):

(e1) positioning the object or patient to be radiographed, (e2) triggering the start of the exposure by the practitioner, (e3) measuring the yield $D_c$ a certain time $t'$ after the start of the exposure, (e4) calculating the equivalent thickness from the measurement of yield $D_c$, (e5) calculating the yield $D_f$ at the film, (e6) estimating the lumination received by the film since the start of the exposure, (e7) calculating the lumination remaining to be acquired to obtain the chosen blackening, (e8) calculating the estimated mA·s remaining to be delivered by the X-ray tube to obtain the chosen blackening, (e9) measuring the mA·s, referenced $mAs_{mes}$, delivered as the case may be since the start of the exposure or since the preceding measurement, (e10) stopping the X-radiation when the $mAs_{mes}$ are greater than or equal to the mA·s computed or, if not, return to the operation (e3).

It must be noted that the term "lumination" is defined as the product of the quantity of light received, for example the illumination EC of the sensitive surface, by the duration of exposure.

The step (e3) consists of measuring the integrated value D given by the device 18 at a certain time $t'$ after the start of the exposure, it being known that the integrator circuit 16 has been reset at zero either, as the case may be, at the start of the exposure, or after the last measurement. The integration time $t'$ corresponds, as the case may be, to the time that has elapsed since the start of the exposure or to the time that has elapsed since the last measurement.

The step (e4) is performed by the microprocessor 19 from the first calibration of the radiology system as described here above: it is governed by the equation (7); a value $E_1$ of the equivalent thickness is then obtained.

It must be observed that, for the second iteration of the method and for the following ones, it is not necessary to perform the step (e4) to the extent that the estimation of the equivalent thickness has been sufficiently precise during the first iteration.

The step (e5) consists of computing the yield of the film $D_f$ corresponding to the thickness $E_1$ in using the function defined by the equation (8), which makes it possible to take account, notably, of the influence of the screen of the receiver. This operation has been described briefly here above.

The step (e6) consists of estimating the lumination $L_f$ received by the film from the start of the exposure in applying the following equation:

$$L_f = L_{am} + D_f \times \delta mA \cdot s \quad (9)$$

This is an equation in which $L_{am}$ is the lumination received by the film before the step (e3) and $\delta mA \cdot s$ is the number of mA·s delivered by the tube during the time $t'$ and is defined by the product of the tube current I by the integration time S.

The step (e7) consists of calculating the lumination remaining to be acquired $L_{ra}$ to obtain the determined blackening; it is given by the equation:

$$L_{ra} = L_{ref} - L_f \quad (10)$$

The step (e8) consists of calculating the mA·s remaining to be delivered to obtain the chosen blackening which is given by the equation:

$$mAs_r = L_{ra}/D_f \quad (11)$$

It is then possible to deduce the number of mA·s delivered during the calculations, referenced $mAs_c$. Then, the mA·s that actually remain to be acquired, referenced $mAs_{ra}$, are defined by:

$$mAs_{ra} = mAs_r - mAs_c \quad (12)$$

where $$mAs_c = I \times t_c \quad (13)$$

with $t_c$ being the time taken for the calculations

The step (e10) consists of making a choice: either to stop the exposure or to continue it according to the value of the mAs remaining to be delivered or, again, the exposure time still to elapse, or to recompute the estimation of the estimated value of the end-of-exposure time.

The end-of-exposure criterion could be the following: If the value:

$$\text{Dif}(mA \cdot s) = mAs_{ra} - mAs_{mes} \quad (15)$$

is nil or below a fixed value $Val_0$, the microprocessor 19 stops the X-radiation by action on the power supply device 15. If not, the step (e3) is returned to.

It is possible to envisage an additional test on the value of the exposure time still to elapse $t_{rc}$ defined by the relationship:

$$t_{rc} = \frac{mAs_{ra}}{I} \quad (14)$$

This additional test consists of not modifying the value of the estimation $mAs_{ra}$ should $t_{rc}$ be smaller than a value $t_o$. Then the end of exposure terminates in an open loop through the continuance of only the end-of-exposure operations, namely the decrementation of the number of mA·s delivered and the stopping of the exposure when this number becomes smaller than or equal to zero. A possible value of $t_o$ is a value substantially equal to the time interval between two measurements corresponding to the step (e3). Thus, in this case, the operation (e10) comprises two tests:

a first test on $mAs_{ra}$ to decide whether or not the exposure must be stopped, then a test on $t_{rc}$ to decide whether to undertake a new estimation of the mAs remaining to be delivered or whether the value mAs$_{ra}$ will remain fixed until the end of the exposure. In the latter case, the end-of-exposure test will be done periodically with the value mAs$_{ra}$.

Besides, the operations for estimating the time still to elapse and that of the interruption of exposure may be separated in order to further refine the precision of the exposer. Thus, the method may be split up as follows: a task T.E. designed to estimate the mA·s remaining to be delivered before the end of the exposure and a task T.C. for interrupting the exposure. These are two independent tasks that occur in parallel.

The task T.E. for estimating the mA·s still to be delivered is constituted by the operations (e3) to (e8) to which there is added an operation (e'9) of conversion of the mA·s into a signal in the units of the cell 12 such that:

$$CE_{target} = mAs_{ra} \times D_c \tag{16}$$

This task of estimation T.E. is renewed periodically during the exposure, for example at the instants $t_1, t_2, \ldots t_n$ which are instants of measurement separated by a period that is at least equal to the computation time $t_c$. At the end of the task of estimation T.E., the target value $CE_{target}$ is updated. This updating should take account of the signal received by the detector cell 12 between the instant of measurement at the start of the operation (e3) and the instant when the value $CE_{target}$ is updated at the end of the operation T.E.

The task (T.C.) of interrupting the exposure is one that consists of decrementing a given value (or target) as a function of the signal actually received by the cell 12. This task interrupts the exposure as soon as the value $CE_{target}$ becomes smaller than or equal to Val$_o$, equal to zero for example.

Thus, the working of the task T.C. can be summarized in the following steps of (or operations for):

(f1) measuring the integrated signal $M_m$ by the cell 12 after a certain time $t_{TC}$;

(f2) decrementing this value to the target value:

$$(CE_{target} - M_m)$$

(f3) stopping the exposure when $(CE_{target} - M_m)$ is lower than Val$_o$, if not return to(f1).

The method that has just been described works accurately to the extent that there is no deviation from the law of reciprocity for the receiver 17 and the detection cell 12. If this is not the case, the operations (e6) and (e8) must be supplemented to take account of it and a coefficient of correction has to be determined by particular measurements and computations. This coefficient of correction is introduced into the equations (9) and (11) where the lumination and yield of the film come into play.

It is thus that the equation (9) and (11) become:

$$L_f = L_{am} + D_{fl} \times \delta mA \cdot s/CNRD \text{ (film dose rate)} \tag{9'}$$

and $$mAs_{ra} = \frac{L_{ra}}{D_{fl}} \times CNRD \text{ (film dose rate)} \tag{11'}$$

with film dose rate=$D_{fl} \times I$ \qquad (17)

CNRD is the function representing the effect of non-reciprocity expressed as a function of the dose rate of photons on the film.

The function CNRD is obtained by a method of calibration that is described in the patent application filed on this date and entitled: METHOD FOR THE DETERMINATION OF THE FUNCTION REPRESENTING THE EFFECT OF NON-RECIPROCITY OF A RADIOGRAPHIC FILM, Ser. No. 07/726,175.

For an understanding of the remaining part of the description, it may be recalled that this calibration method consists, first of all, in determining the coefficients of non-reciprocity of the film as a function of the period of exposure $t_i$, said coefficients being referenced CNRT ($t_i$). This function CNRT is determined experimentally and may be represented by an analytical function.

More precisely, the method consists in the determination, for various values IR$_i$ of the intensity of the radiation, of the value $t_i$ of the time of exposure needed to obtain a fixed optical density DO$_{refo}$ of the film, for example DO$_{refo}=1$, and in the reading of the values given by the integrator circuit 16 for the different exposure times $t_i$, namely values that shall be called M ($t_i$).

These values are compared with a reference value M ($t_{ref}$), which is, for example, the value corresponding to an exposure time of one second, in computing the ratio $$\frac{M(t_i)}{M(t_{ref})} \tag{29}$$

It is this ratio that determines the coefficient of non-reciprocity in time CNRT ($t_i$) for the exposure time $t_i$.

Another way to determine the coefficients CNRT ($t_i$) shall be described further below.

These coefficients CNRT ($t_i$) are related to one another as a function of the exposure time by the curve of FIG. 3 in the case, for example of an optical density DO$_{refo}=1$ and a reference exposure time $t_{ref}=1$ second. This curve shows that the lumination needed to achieve the desired optical density increases with the exposure time. It is thus that, in this example, the ratio between the energies for the two exposure times of 50 ms and 6.5 s is of the order of 1.6.

The curve of FIG. 3 may be modelized by means of a function having the form:

$$CNRT(t) = A_o + A_1 \log t + A_2 [\log t]^2 \tag{18}$$

the parameters $A_0$, $A_1$ and $A_2$ of which are estimated from the measurement points by a least square error method of estimation.

In principle, the Schwarzschild effect that is taken into account in the equations (9') and (11') could be modelized by the function CNRT. The interest of using the function CNRD indexed in film dose rate is that it is possible to take account of the variations of the anode current. Hence, an automatic exposer that uses the function CNRD according to the equations (9') and (11')

has, for example, the advantage wherein the tube can work in decreasing load.

To go from the time-indexed coefficients CNRT (t) to the rate-indexed coefficients CNRD (d), it is necessary to take account of the fact that the coefficients CNRT (t) have been determined by measurements with variable exposure times under conditions where the values of the photon dose rate on the film are not necessarily known. If the film dose rate $d_i$ is measured for each exposure time $t_i$, the value of the coefficient CNRD (di) for di will be equal to that of the coefficient CNRT ($t_i$) for the corresponding exposure time $t_i$ according to the relationship :

$$CNRD (d_i) = CNRT (t_i) \qquad (19)$$

These different values of CNRD ($d_i$) are related to one another by a curve (FIG. 4) as a function of the reciprocal 1/d of the dose rate. This curve may be modelized by means of a function having the form :

$$CNRD (d) = A'_o + A'_1 \log 1/d + A'_2 [\log 1/d] \qquad (20)$$

It may be the case that the values $d_i$ are not given by the calibration, especially because they are expressed in the measurement unit of the cell 12 which is not necessarily the one used in the calibration. Thus, in general, the values $d_i$ must be linked to the known values $t_i$ by the relationship:

$$L_{ref} \times CNRT (t_i) = d_i \times t_i \qquad (21)$$

or again :

$$d_i = \frac{L_{ref} \times CNRT (t_i)}{t_i} \qquad (22)$$

It is recalled here that $L_{ref}$ is the lumination received by the film under fixed and known radiological conditions when the film attains a given blackening and when the non-reciprocity effect is corrected.

To finalize the definition of the function CNRD as well as to explain the last calibration of the method, there remains to be explained the method used to assess the reference lumination.

This method is described in the above-mentioned patent application, entitled : METHOD FOR THE ESTIMATION AND CALIBRATION OF THE LUMINATION RECEIVED BY A RADIOGRAPHIC FILM.

The reference lumination depends on the optical density to be obtained on the film. To determine this lumination, the first step is to make a sensitogram of the type of film used, then a shot must be taken under determined radiological conditions with a known thickness standard.

These determined radiological conditions are, for example, a reference optical density $DO_{refo}$ chosen as a function of the practitioner's usual practices, for example $DO_{refo} = 1$ a thickness standard $E_o$, a supply voltage $V_o$, a value of the exposure time $t_o$, a value of the product $I_o \times t_o$, For this shot, the optical density $DO_m$ as well as the values $M_o$, $I_o$, to are measured. This makes it possible to compute the equivalent thickness $E_p$ by means of the equation (7). The yield $D_f$ on the film is then computed by means of the equation (6): this makes it possible to compute the lumination received by the film $L_{film}$ by the formula:

$$L_{film} = D_f \times I_o \times t_o \qquad (23)$$

The reference optical density $DO_{refo}$ makes it possible to compute the illumination step corresponding to $DO_{refo}$ on the sensitometric curve of the film used, (FIG. 5), this curve having been plotted by means of a sensitograph and a densitometer. This makes it possible to take account of the characteristics of the developing machine used. The curve is recorded, for example, in the form of a function in the microprocessor 19 (FIG. 1).

Figure 5:
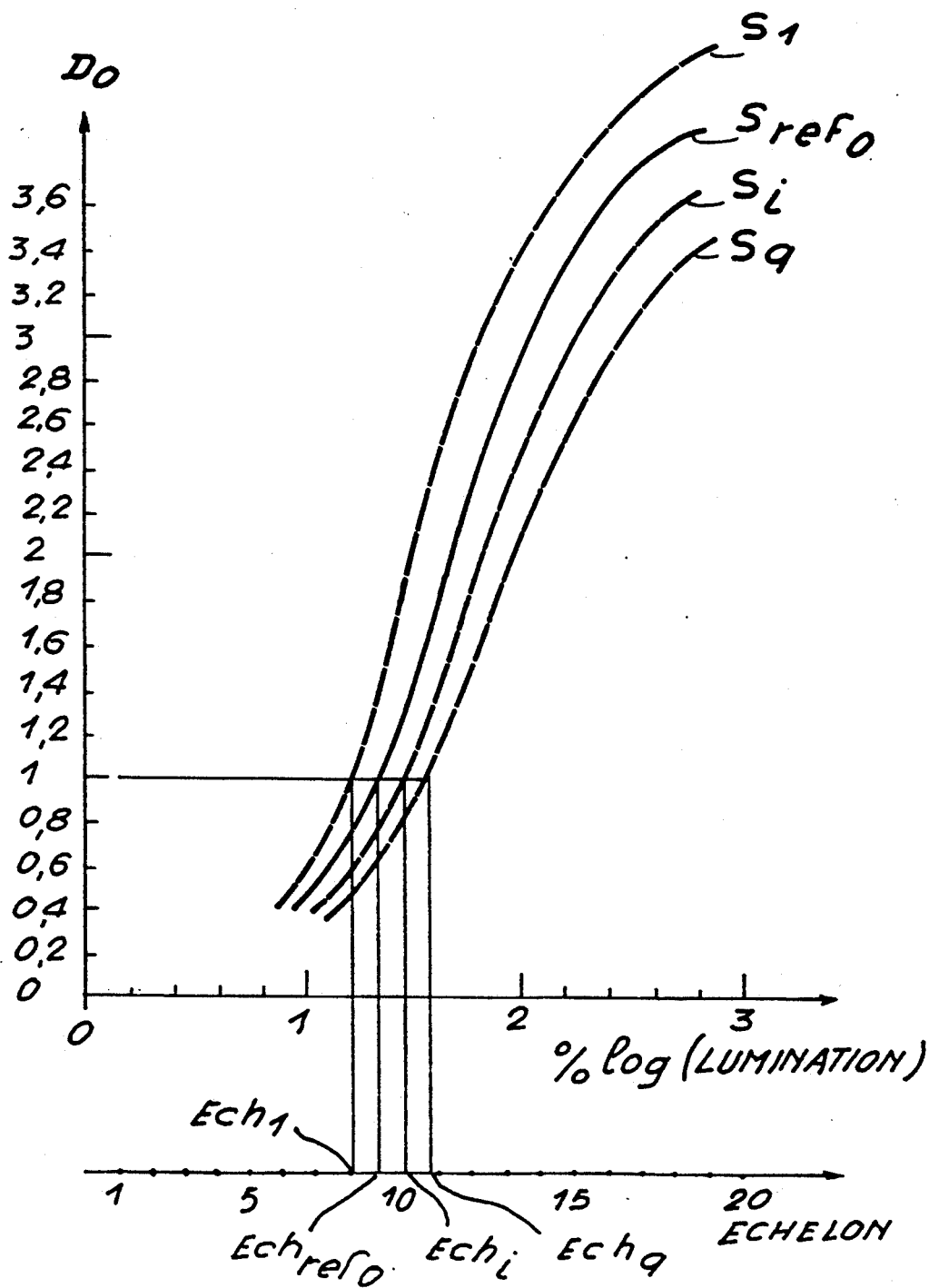
FIG. 5 is a graph showing curves of variation of the optical density of a radiographic film as a function of the lumination.

The optical density measured $DO_m$ enables the computation of the measurement step $Ech_m$ which is the value of the illumination step corresponding to $DO_m$ on the sensitometric curve (FIG. 5).

With the values $L_{film}$ of the lumination on the film, the reference step $Ech_{ref}$ and the measurement step $Ech_m$, it is possible to compute the reference lumination $L_{ref}$ to obtain the optical density $DO_{refo}$ by using the equation that defines the change in scale between the lumination and the illumination step of the x-axis of the sensitometric curve (FIG. 5), that is :

$$Ech_m = Ech_{ref} + K \cdot \log_{10} \left[ \frac{L_{film}}{L_{ref}} \right] \qquad (24)$$

From this equation (24), we derive :

$$L_{ref} = L_{film} \times \exp \left[ \log_{10} \left[ \frac{Ech_{ref} - Ech_m}{K} \right] \right] \qquad (25)$$

with $K = 2/\log_{10} (2)$ \qquad (26)

The sensitometric constant K corresponds to the scale chosen for the illumination steps.

The value $L_{ref}$ depends on $t_o$ through $L_{film}$ by the equations (23) and (25). Thus, the value $L_{ref}$ is sensitive to the non-reciprocity effects of the film. To correct the influence of non-reciprocity on the value of $L_{ref}$, it is enough to use, in the equation (23), the value $L_{film}$ defined by :

$$L_{film} = \frac{D_f \times I_o \times t_o}{CNRT (t_o)} \qquad (23')$$

This reference lumination $L_{ref}$ is the one that must be used in the equation (10) to obtain the reference optical density $DO_{refo}$ and the formula (25) shows that it depends, notably, on the difference between the reference step and the measurement step.

The knowledge of the lumination received by the film provides for knowing $d_i$ by the application of the formula (22) and for deducing CNRD ($d_i$) therefrom by the formula (20).

For an optical density of the radiographic film other than $DO_{refo} = 1$, the above-described operations have to be repeated so as to determine the new values of CNRT ($t_i$) and of $L_{ref}$.

In order to simplify these operations, the coefficients CNRT ($t_i$) may be obtained by performing the following steps of:

(g1) making, by means of a variable time sensitograph, a first sensitogram $S_{refo}$ (FIG. 5) when the exposure time is set for a reference time $t_{refo}$;

(g2) making, by means of a variable time sensitograph, q sensitograms $S_1$ to $S_q$ (FIG. 5) for different exposure times $t_i$;

(g3) choosing a reference optical density $DO_{refo}$, for example $DO_{refo}=1$ (g4) measuring, on each sensitogram, the illumination step $Ech_{refo}$, $Ech_1$ ... $Ech_i$ ... $Ech_1$ corresponding to the optical density $DO_{refo}=1$ (g5) calculating the coefficient CNRT ($t_i$) by the equation:

$$CNRT(t_i) = \exp\left[\log_{10}\left[\frac{Ech_{refo} - Ech_i}{K}\right]\right] \quad (28)$$

If the practitioner decides to work at a different optical density, it is proposed, in order to avoid the above-described calibration, to use the optical density deliberately corrected for the blackening $DO_{cvn}$. Then, the reference lumination $L_{ref}$ used in the equation (10) should be replaced by the corrected lumination $L_{cvn}$ which is expressed by:

$$L_{cvn} = L_{ref} \times \exp[CVN/\Gamma \times P \times \text{Log}(10)] \quad (27)$$

where

CVN is the deliberate correction of blackening expressed by a whole number from $-10$ to $+10$ for example, P is the elementary step in optical density, for example 0,1, $\Gamma$ is the slope of the linear part of the sensitometric curve (FIG. 5).

The method that has just been described shows that its implementation calls for a certain number of calibrations that are, briefly, the following:

(a) the calibration of the radiological system so as to determine the analytical models $$D_{se} = f'(V_m, E_p) \quad (4)$$

with cartridge without screen and $$D_c = f''(V_m, E_p) \quad (6)$$

$$E_p = g''(V_m, D_c) \quad (7)$$

with cartridge and screen;

The difference $D_f = (D_{se} - D_c)$ (equation (8)) will make it possible to deduce the yield absorbed by the screen;

(b) the calibration of the film so as to determine the law of non-reciprocity CNRT (t) expressed as a function of time; this law will be used to determine the law of non-reciprocity CNRD (d) expressed as a function of the dose rate;

(c) the calibration of the reference lumination $L_{ref}$.

When these different calibrations have been performed, the method consists of the following steps of:

(d) choosing, by the practitioner, the blackening value or of the value of the deliberate correction of blackening so as to determine the target lumination $L_{cvn}$ that should be received by the film under fixed reference conditions to arrive at the chosen blackening (or optical density). The lumination $L_{cvn}$ is computed from the equation (27) where the lumination $L_{ref}$ is determined by the calibration (c) and the equations (25) and (26);

(e1) positioning the object to the radiographed, (e2) triggering the start of the exposure by the practitioner (e3) measuring after a time t' the yield $D_{c1}$ at the cell 12;

(e4) measuring the equivalent thickness $E_1$ by the equation (7);

(e5) calculating the yield $D_{f1}$ at the film for the thickness $E_1$ by the equation (8);

(e6) calculating the lumination $L_f$, received by the film, by the equation;

$$L_f = L_{am} + D_{f1} \times \delta mA \cdot s/CNRD \text{ (film dose rate)} \quad (9')$$

(e7) calculating the lumination $L_{ra}$ remaining to be acquired to obtain the blackening (or optical density) chosen by the equation $$L_{ra} = L_{cvn} - L_f \quad (10)$$

(e8) calculating the estimated mA·s remaining to be delivered $mAs_{ra}$ to obtain the blackening (or optical density) by the equation:

$$mAs_{ra} = L_{ra}/D_{f1} \times CNRD \text{ (film dose rate)} \quad (11')$$

(e9) calculating the mA·s delivered since the start of the operation (e3);

(e10) stopping the exposure when the mA·s measured in (e9) are equal to or greater than $mAs_{ra}$.

or returning to the step (e3) when the mA·s measured in (e9) are less than $mAs_{ra}$.

The description of the method that has just been given corresponds to a certain configuration of the radiology system. Should it be possible for this system to assume several configurations involving, for example, the choice of:

the material of the anode the dimensions of the focus, the spectrum modifying filter, the collimation, the presence or absence of a diffusion-preventing screen, the type of image receiver, the type of detection cell, it is necessary to perform calibrations (a), (b) and (c) for each of these configurations. The number of these calibrations may be reduced by taking account of the similarities of behavior from one configuration to another, as described for the calibration (a) in U.S. Pat. application Ser. No. 07/535 520 filed on the Jun. 8, 1990.

When the practitioner implements the method, he defines the configuration, and the characteristics of this configuration are transmitted to the microprocessor 19 so that the latter uses the corresponding models.

The method according to the invention has been described in its application to a receiver 17 of the film/screen couple type. It can also be implemented in the case of a receiver 17 having only a film sensitive to X-radiation. With such a film, the calibrations of the operations (a) and (b) become:

(a') the calibration of the radiological system so as to determine the analytical model $$D'_f = f'''(V_m, E_p) \quad (30)$$

with the film as the image receiver.

In the unfolding of the method, the modifications are as follows:

(e3) becomes (e'3): measuring after a time t' of the yield $D'_{fl}$ at the cell 12;

(e4) and (e5) are eliminated and the steps (e6) to (e8) are modified in the following way:

(e'6) computing the lumination $L'_f$ received by the film by the equation:

$$L'_f = L_{am} + D'_{fl} \times \delta mA \cdot s / CNRD \text{ (film dose rate)} \quad (9'')$$

(e'7) calculating the lumination $L'_{ra}$ remaining to be acquired to obtain the blackening (or optical density) chosen by the equation $$L'_{ra} = L_{ref} - L'_f \quad (10'')$$

(e'8) calculating the estimated mA·s remaining to be delivered $mAs'_{ra}$ to obtain the blackening (or optical density) by the equation:

$$mAs'_{ra} = L'_{ra}/D'_{fl} \times CNRD \text{ (film dose rate)} \quad (11'')$$

The other steps (e9) and the ones that follow remain unchanged.

Besides, it must be noted that the sensitograph may, in this case, be of the X-ray emission type.

Furthermore, with a receiver such as this, having no intensifier screen, the detection cell 12 may be placed either behind the receiver 17, as in the case of the film/screen type receiver, or before the receiver 17 if the energy of the radiation allows it.

Figure 6:
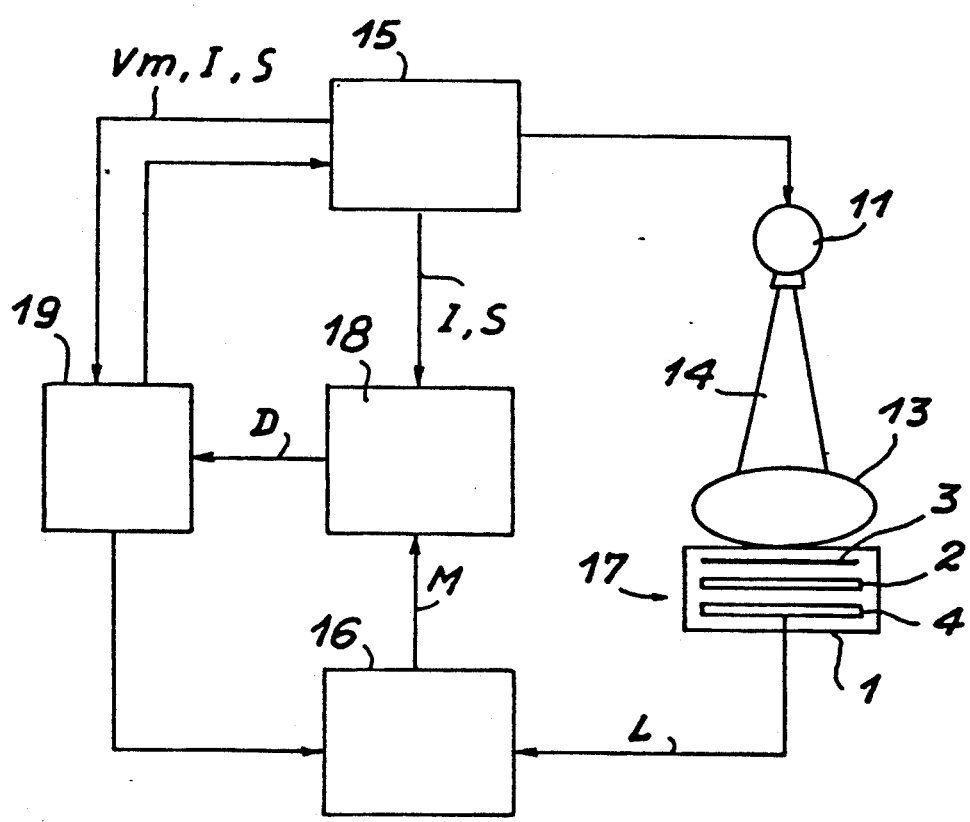
FIG. 6 is a block diagram of a radiology system, similar to the one of FIG. 1 but in which the detection cell is incorporated in the receiver and is subject to light emitted by the screen.

The method according to the invention has been described in an application to a radiology system (FIG. 1) in which the X-ray detection cell 12 is disposed outside the receiver but said method may be applied to a radiology system (FIG. 6) in which said detection cell is incorporated inside the receiver 17 as the element bearing the reference numeral 4. Then, the receiver 17 comprises a film 3, an intensifying screen below the film 3 and said new detection cell 4 below the screen 2.

Such a new detection cell 4 is of the type described in French patent application 89 05668 filed on the Apr. 28, 1989 and entitled: "An X-ray cassette incorporating an automatic exposure detector cell".

This new detection cell detects and measures the light emitted by the screen 2 as compared to the detection cell 12 which detects and measures the X-radiation behind the receiver. As a result, there is no need to perform the first and second calibrations of the method described above, which are directed to take account of the attenuations of the X-rays by the film and the screen. Moreover, corresponding steps (e4) and (e5) are no longer needed.

This leads to a modified method which comprises the following steps of (or operations for):

(a) determining by calibration the reference lumination $L_{ref}$ which must be received by the film, under fixed reference conditions, to achieve the blackening (or optical density) chosen as a reference value by the practitioner;

(b1) positioning the object to be radiographed;

(b2) triggering the start of the exposure by the practitioner;

(b3) measuring yield $D_{fl}$ at a certain time t' after the start of the exposure;

(b4) calculating the lumination $L_f$ received by the film according to the equation:

$$L_f = L_{am} + D_{fl} \times \delta mA \cdot S \quad (9)$$

(b5) calculating the lumination $L_{ra}$ remaining to be acquired to obtain the blackening for optical density determined by the equation:

$$L_{ra} = L_{ref} - L_f \quad (10)$$

(b6) calculating the estimated mA·s remaining to be delivered $mAs_r$ to obtain the blackening (or optical density) determined by the equation:

$$mAs_r = L_{ra}/D_{fl} \quad (11)$$

(b7) measuring the mA·s delivered $mAs_{mes}$ from the start of step (b3);

(b8) —stopping the exposure when the mA·s measured $mAs_{mes}$ in step (b7) are equal to or greater than $mAs_r$, —or returning to step (b3) when the mA·s measured in step (b7) are smaller than $mAs_r$.

The use of such a detection cell 4 inside the receiver 17 makes the method simpler to implement.

It must be noted that this simpler method, which can be implemented when a light detector cell 4 inside the receiver 17 is used, can make use of all features related to the first method described above inasmuch as they are related to steps (a''), (b1) to (b8).

What is claimed is:

1. A method for automatically determining the exposure time of a radiographic film in a system of radiology designed to examine an object that includes an X-ray tube, the supply voltage V of which may assume various values $V_m$, with continuous or discrete variation, said X-ray tube emitting an X-ray beam in the form of pulses of variable duration S towards the object to be examined, an image receiver for detecting the X-radiation that has crossed the object to form an image of said object, said receiver being constituted by at least one intensifier screen and a film sensitive to the light emitted by said screen, a cell for the detection of the X-rays that have crossed the object to be examined, placed behind the image receiver, for converting a physical variable, characterizing the X-ray beam into a measurement signal L, an integrator circuit that integrates the measurement signal L for the duration S of the exposure to produce a signal M, and a device to compute the yield D given by the ratio of M to the product I×S (mA·s) of the anode current I of the tube by the duration S of the exposure, wherein said method includes the following operations:

(a) a first calibration of the radiology system by means of objects with a thickness $E_p$ by using a receiver without the intensifier screen or screens so as to determine the yield $D_{se}$ from the function:

$$D_{se}=f'(V_m, E_p) \qquad (4)$$

and the thickness $E_p$ from the inverse function:

$$E_p=g'(V_m, D_{se}) \qquad (5)$$

(b) a second calibration of the radiology system by means of the objects with a thickness $E_p$ by using a receiver with an intensifier screen so as to determine the yield $D_c$ from the function:

$$D_c=f''(V_m, E_p) \qquad (6)$$

the thickness $E_p$ from the inverse function:

$$E_p=g''(V_m, D_c) \qquad (7)$$

and compute the yield on the film $D_f$ function:

$$D_f=f'(V_m, E_p)-f''(V_m, E_p) \qquad (8)$$

(c) a third calibration to determine the reference lumination $L_{ref}$ that must be received by the film, under fixed reference conditions, to achieve the blackening (or optical density) chosen as a reference value comprising the following steps of:
(e1) positioning the object to be radiographed;
(e2) triggering the start of the exposure;
(e3) measuring the yield $D_{c1}$ at a certain time $t'$ after the start of the exposure;
(e4) measuring the equivalent thickness $E_1$ by the equation $g''(V_m, D_c)$;
(e5) calculating the yield $D_{f1}$ at the level of the film for the thickness $E_1$ by $f'(V_m, E_p)-f''(V_m, E_p)$;
(e6) calculating the lumination $L_f$ received by the film from the illumination received by the film before step (e3) $L_{am}$ and the number of mA·s delivered by the tube during $t'$, $\delta$mA·s according to the equation:

$$L_f=L_{am}+D_{f1}\times\delta mA\cdot s \qquad (9)$$

(e7) calculating the lumination $L_{ra}$ remaining to be acquired to obtain the blackening (or optical density) determined by the equation:

$$L_{ra}=L_{ref}-L_f \qquad (10)$$

(e8) calculating the estimated mA·s remaining to be delivered $MaS_r$ to obtain the blackening (or optical density) determined by the equationL $$mAs_r=L_{ra}/D_{f1} \qquad (11)$$

(e9) measuring the mA·s delivered $mAs_{mes}$ from the start of the operation (e3);
(e10) stopping the exposure when the mA·s measured $mAs_{mes}$ are equal to or greater than $mAs_r$, or a return to the step (e3) when the mA·s measured are smaller than $mAs_r$.

2. A method according to claim 1, wherein the second calibration (b) is supplemented by a determination of the equivalent thickness (sup.filter) due to the additional filtration between the intensifier screen and the detection cell which is subtracted from $E_p$ in the equation (8) as $(E_p - \text{sup.filter})$.

3. A method according to claim 1 or 2, wherein the step of stopping the exposure includes a substep of calculating the remaining exposure time $t_r$ such that $$t_r = \frac{mAs_r}{I}$$

so as to end the exposure in an open loop and the exposure will be stopped when the time $t_r$ has elapsed.

4. A method according to claim 1 or 2, wherein the step (e8) further includes a step of calculating the mA·s delivered $(mAs_c)$ during a duration $t_c$ of the steps (e4) to (e8) defined by the equation:

$$mAs_c = I \times t_c \qquad (13)$$

so as to determined the real value of the mA·s remaining to be acquired $(mAs_{ra})$ such that:

$$mAs_{ra}=mAs_r-mAs_c \qquad (12)$$

5. A method according to claim 4, wherein the step (e10) further includes a step of calculating the remaining exposure time $t_{rc}$, such that $$t_{rc} = \frac{mAs_{ra}}{I} \qquad (14)$$

so as to end the exposure when $t_{rc}$ is smaller than a value $t_o$ corresponding to the interval of time between two successive steps (e3).

6. A method according to claim 1, wherein the steps (e6) and (e8) take account of the effect of non-reciprocity such that:

$$L_f=L_{am}+D_{f1}\times\delta mA\cdot s/CNRD \text{ (film dose rate)} \qquad (9')$$

and $$mAs_{ra} = \frac{L_{ra}}{D_{f1}} \times CNRD \text{ (film dose rate)} \qquad (11')$$

wherein CNRD (film dose rate) is the coefficient of non-reciprocity indexed as a function of the film dose rate of the receiver such that:

$$\text{film dose rate}=D_{f1}\times I \qquad (17)$$

7. A method according to claim 6 wherein the coefficient CNRD (film dose rate) is obtained by performing the following steps of (or operations for):
measuring the coefficients of non-reciprocity CNRT $(t_i)$ of the film/screen couple as a function of the exposure time $(t_i)$,
measuring for each exposure time $(t_i)$ of the film dose rate $d_1$,
determining the function of modelization of the coefficients CNRD $(d_i)$ such that:

$$CNRD(d)=A'_0+A'_1\log 1/d+A'_2[\log 1/d]^2 \qquad (20)$$

which makes it possible to determine the coefficient corresponding to a give film dose rate.

8. A method according to claim 7, wherein the film dose rate d is measured by the cell.

9. A method according to claim 7, wherein the film dose rate $d_i$ is given by the formula:

$$d_i = \frac{L_{ref} \times CNRT(t_i)}{t_i} \quad (22)$$

10. A method according to claim 7 or 9, wherein the coefficients of non-reciprocity CNRT $(t_i)$ as a function of the exposure time $(t_i)$ are obtained by performing the following steps of (or operations for):
 (a1) modifying the tube heating current so as to obtain different values of said current,
 (a2) reading the values $M(t_i)$ given by the integrator circuit for different exposure times so as to obtain an optical density $DO_1$ of the film
 (a3) calculation of the ratio $$\frac{M(t_i)}{M(t_{ref})} \quad (29)$$

which gives the coefficient CNRT $(t_i)$ with M $(t_{ref})$ the value M $(t_i)$ for $t_i = t_{ref}$.

11. A method according claim 7 or 9, wherein the coefficients CNRT $(t_i)$ are obtained by performing the following steps of (or operations for):
 (g1) making, by means of a variable time sensitograph, a first sensitogram $S_{refo}$ when the exposure time is set for a reference time $t_{refo}$;
 (g2) making, by means of a variable time sensitograph, q sensitograms $S_1$ to $S_q$ for different exposure times $t_i$;
 (g3) choosing a reference optical density $DO_{refo}$;
 (g4) measuring, on each sensitogram, the illumination step $Ech_{refo}$, $Ech_1$...$Ech_i$...$Ech_q$ corresponding to the optical density $DO_{refo}$;
 (g5) calculating the coefficient CNRT $(t_i)$ by the equation:

$$CNRT(t_i) = \exp\left[\log_{10}\left[\frac{Ech_{refo} - Ech_i}{K}\right]\right] \quad (28)$$

12. A method according to claim 10, further comprising an operation for the modelization of the coefficients CNRT $(t_i)$ in the form of an analytical model by the function:

$$CNRT(t) = A_0 + A_1 \log t + A_2[\log t]^2 \quad (18)$$

13. A method according to claim 1, wherein the operation (c) for calibrating the reference lumination includes the following steps of:
 taking a shot under determined radiological conditions for a reference optical density $DO_{refo}$, a thickness standard $E_o$, a supply voltage $V_o$, an exposure time $t_o$ and a value of the product $I_o \times t_o$;
 measuring of the yield $D_o$;
 calculating the equivalent thickness $E_{po}$ by the formula:

$$E_{po} = g''(V_o, D_o) \quad (7)$$

the computation of the yield $D_{fo}$ on the film by the formula:

$$D_{fo} \times I_o \times t_o \quad (23)$$

calculating the illumination step $Ech_{ref}$ corresponding to the reference optical density $DO_{refo}$ by means of the sensitometric curve;
measuring the optical density $DO_m$ of the shot obtained and the computation of the illumination step $Ech_m$ by means of the sensitometric curve;
calculating the reference lumination $L_{ref}$ by the formula:

$$L_{ref} = L_{film} \times \exp\left[\log_{10}\left[\frac{Ech_{ref} - Ech_m}{K}\right]\right] \quad (25)$$

14. A method according to claim 13 wherein, for the computing the yield $D_{fo}$ on the film by the equation (8), (sup.filter)$_2$ the equivalent thickness due to the additional filtration resulting from the attenuation between the intensifier screen and the detection cell is subtracted from the equivalent thickness $E_{po}$.

15. A method according to claim 13, or 14, wherein the luminance on the film is computed by the formula:

$$L_{film} = \frac{D_{fo} \times I_o \times t_o}{CNRT(t_o)} \quad (23')$$

16. A method according to claim 1, wherein the reference lumination $L_{ref}$ represents a corrected lumination $L_{cvn}$ so as to obtain a optical density such that:

$$L_{cvn} = L_{ref} \times \exp[CVN/\Gamma \times P \times \text{Log}(10)] \quad (27)$$

where
 CVN is the deliberate correction of blackening expressed by a whole number for example,
 P is the elementary step in optical density,
 $\Gamma$ is the slope of the linear part of the sensitometric curve.

17. A method for automatically determining the exposure time of a radiographic film in a system of radiology designed to examine an object that includes an X-ray tube, the supply voltage V which may assume various values $V_m$, with continuous or discrete variation, said X-ray tube emitting an X-ray beam in the form of pulses of variable duration S towards the object to be examined, a receiver of the X-radiation that has crossed the object to form an image of said object, said receiver being constituted by at least one intensifier screen, a film sensitive to the light emitted by said screen and a cell for the detection of the light emitted by said screen, that enables the conversion of a physical variable, characterizing the X-ray beam, into a measurement signal L, an integrator circuit that integrates the measurement signal L for the duration S of the exposure and gives a signal M, and a device to compute the yield D given by the ratio of M to the product $I \times S$ (mA·s) of the anode current I of the tube by the duration S of the exposure, wherein said method includes the following steps of:
 (a) determining by calibration the reference lumination $L_{ref}$ that must be received by the film, under fixed reference conditions, to achieve the blackening chosen as a reference value;
 (b1) positioning the object to be radiographed;
 (b2) triggering the start of the exposure by the practitioner;
 (b3) measuring the yield $D_{f1}$ at a certain time $t'$ after the start of the exposure;

(b4) calculating the lumination $L_f$ received by the film from the illumination received from the film before step (b3) and from the number of mA·s delivered by the tube during t', δmA·s, according to the equation:

$$L_f = L_{am} + D_{fl} \times \delta mA \cdot s \tag{9}$$

(b5) calculating the lumination $L_{ra}$ remaining to be acquired to obtain the determined blackening (or optical density) by the equation:

$$L_{ra} = L_{ref} = L_f \tag{10}$$

(b6) calculating the estimated mA·s remaining to be delivered $mAs_r$ to obtain the determined blackening (or optical density) by the equation:

$$mAs_r = L_{ra}/D_{fl} \tag{11}$$

(b7) measuring the mA·s delivered $mAs_{mes}$ from the start of the operation (b3);

(b8) stopping the exposure when the mA·s measured $mAs_{mes}$ (in step (b7)) are equal to or greater than $mAs_r$, or returning to the step (b3) when the mA·s measured in step (b7) are smaller than $mAs_r$.

18. A method according to claim 17, wherein the step (b6) further includes a step of calculating the mA·s delivered ($mAs_c$) during a duration $t_c$ of the steps (b4) to (b6) defined by the equation:

$$mAs_c = I \times t_c \tag{13}$$

so as to determined the real value of the mA·s remaining to be acquired ($mAs_{ra}$) such that:

$$mAs_{ra} = mAs_r - mAs_c \tag{12}$$

19. A method according to claim 18, wherein the step (b8) further includes a step of calculating the remaining exposure time $t_{rc}$, such that $$t_{rc} = \frac{mAs_{ra}}{I} \tag{14}$$

so as to end the exposure when $t_{rc}$ is smaller than a value $t_o$ corresponding to the interval of time between two successive steps (b3).

20. A method according to claim 18, wherein the steps (b4) and (b6) further comprise steps to take account of the effect of non-reciprocity which include:

$$L_f = L_{am} + D_{fl} \times \delta mA \cdot s / CNRD \text{ (film dose rate)} \tag{9'}$$

and $$mAs_{ra} = \frac{L_{ra}}{D_{fl}} \times CNRD \text{ (film dose rate)} \tag{11'}$$

formulae in which CNRD (film dose rate) is the coefficient of non-reciprocity indexed as a function of the film dose rate of the receiver such that:

$$\text{film dose rate} = D_{fl} \times I \tag{17}$$

21. A method according to claim 20, wherein the coefficient CNRD (film dose rate) is obtained by performing the following steps of:

measuring the coefficients of non-reciprocity CNRT ($t_i$) of the film/screen couple as a function of the exposure time ($t_i$), measuring for each exposure time ($t_i$) of the film dose rate $d_i$, determining the function of modelization of the coefficients CNRD ($d_i$) such that:

$$CNRD(d) = A'_0 + A'_1 \log 1/d + A'_2 [\log \tfrac{1}{d}]^2 \tag{20}$$

where $A'_0$, $A'_1$ and $A'_2$ are estimates from measurement points of least square errors which makes it possible to determine the coefficient corresponding to a given film dose rate.

22. A method according to claim 21, wherein the film dose rate d is measured by the cell.

23. A method according to claim 22, wherein the film dose rate $d_i$ is given by the formula:

$$d_i = \frac{L_{ref} \times CNRT(t_i)}{t_i} \tag{22}$$

24. A method according to claim 17, wherein the operation (a) for calibrating the reference lumination includes the following steps of:

taking a shot under determined radiological conditions for a reference optical density $DO_{refo}$, a thickness standard $E_o$, a supply voltage $V_o$, an exposure time $t_o$ and a value of the product $I_o \times t_o$;

measuring of the yield $D_{fo}$;

calculating the luminance $L_{film}$ on the film by the formula:

$$D_{fo} \times I_o \times t_o \tag{23}$$

calculating the illumination step $Ech_{ref}$ corresponding to the reference optical density $DO_{refo}$ by means of the sensitometric curve;

measuring the optical density $DO_m$ of the shot obtained and the computation of the illumination step $Ech_m$ by means of the sensitometric curve;

calculating the reference lumination $L_{ref}$ by the formula:

$$L_{ref} = L_{film} \times \exp\left[\log_{10}\left[\frac{Ech_{ref} - Ech_m}{K}\right]\right] \tag{25}$$

with $K = 2/\log_{10}$. (2)

25. A method according to claim 24, wherein the luminance on the film $L_{film}$ is calculated by the formula:

$$L_{film} = \frac{D_{fo} \times I_o \times t_o}{CNRT(t_o)} \tag{23'}$$

where CNRT ($t_o$) is the value of CNRT at time $t_o$.

26. A method according to claim 24, wherein the reference lumination $L_{ref}$ is corrected lumination $L_{cvn}$ so as to obtain a different blackening (or optical density) such that:

$$L_{cvn} = L_{ref} \times \exp[CVN/\Gamma \cdot P \times \log(10)] \tag{27}$$

where

CNV is the deliberate correction of blackening expressed by a whole number for example, P is the elementary step in optical density, Γ is the slope of the linear part of the sensitometric curve.

27. A method for automatically determining the exposure time of a radiographic film in a system of radiology designed to examine an object that includes an X-ray tue, the supply voltage V which may assume various values $V_m$, with continuous or discrete variation, said X-ray tube emitting an X-ray beam in the form of pulses of variable duration S towards the object to be examined, an image receiver of the X-radiation that has crossed the object to form an image of said object, said receiver being constituted by at least one intensifier screen, a film sensitive to the light emitted by said screen and a cell for the detection of the light emitted by said screen, that enables the conversion of a physical variable, characterizing the X-ray beam, into a measurement signal L, an integrator circuit that integrates the measurement signal L for the duration S of the exposure and gives a signal M, and a device to compute the yield D given by the ratio of M to the product I×S (mA·s) of the anode current I of the tube by the duration S of the exposure, wherein said method includes the following steps of:

(a) determining by calibration the reference lumination $L_{ref}$ that must be received by the film, under fixed reference conditions, to achieve the blackening (or optical density) chosen as a reference value:

b1) positioning the object to be radiographed;

b2) triggering the start of the exposure;

b3) measuring the yield $D_{fl}$ at a certain time t' after the start of the exposure;

b4) calculating the lumination $L_f$ received by the film from the illumination received from the film before step B3 and from the number of mA·s delivered by the tue during t', δmA·s according to the equation:

$$L_f = L_{am} + D_{fl} \times \delta mA\cdot s \quad (9)$$

(b5) calculating the lumination $L_{ra}$ remaining to be acquired to obtain the blackening (or optical density) determined by the equation:

$$L_{ra} = L_{ref} - L_f \quad (10)$$

(b6) calculating the estimated mA·s remaining to be delivered $mAs_r$ to obtain the blackening (or optical density) determined by the equation:

$$mAs_r = L_{ra}/D_{fl} \quad (11)$$

(b7) measuring the mA·s delivered $mAs_{mes}$ from the start of the operation (b3);

(b8) calculating the remaining exposure time $t_r$ such that $$t_r = \frac{mAs_r}{I}$$

so as to end the exposure in an open loop so that the exposure will be stopped when the time $t_r$ has elapsed.

28. A method for automatically determining the exposure time of a radiographic film in a system of radiology designed to examine an object that includes an X-ray tue, the supply voltage V which may assume various values $V_m$, with continuous or discrete variation, said X-ray tube emitting an X-ray beam in the form of pulses of variable duration S towards the object to be examined, an image receiver of the X-radiation that has crossed the object to form an image of said object, said receiver being constituted by at least one intensifier screen, a film sensitive to the light emitted by said screen and a cell for the detection of the light emitted by said screen, that enables the conversion of a physical variable, characterizing the X-ray beam, into a measurement signal L, an integrator circuit that integrates the measurement signal L for the duration S of the exposure and gives a signal M, and a device to compute the yield D given by the ratio of M to the product I×S (mA·s) of the anode current I of the tube by the duration S of the exposure, wherein said method includes the following steps of:

(a) determining by calibration of the reference lumination $L_{ref}$ that must be received by the film, under fixed reference conditions, to achieve the blackening (or optical density) chosen as a reference value:

(b1) positioning the object to be radiographed;

(b2) triggering the start of the exposure;

determining an estimation (T.E.) of the mA·s remaining to be delivered, and converting the mA·s into a signal in the units of the cell such that:

$$CE_{target} = mAs_{ra} \times D_c \quad (16)$$

interrupting (T.C.) the exposure which consists in decrementing the target value $CE_{target}$ by the signals received by the cell and in terminating the exposure when the decremented value becomes smaller than or equal to a reference value $Val_o$.

29. A method according to claim 28, wherein the task of estimation (T.E.) is renewed periodically during the exposure at instants $t_1$, $t_2$...$t_n$ separated by a duration that is at least equal to a calculating time $t_c$.

30. A method for automatically determining the exposure time of a radiographic film in a system of radiology designed to examine an object that includes an X-ray tue, the supply voltage V which may assume various values $V_m$, with continuous or discrete variation, said X-ray tube emitting an X-ray beam in the form of pulses of variable duration S towards the object to be examined, an image receiver of the X-radiation that has crossed the object to form an image of said object, said receiver being constituted by at least one intensifier screen, a film sensitive to the light emitted by said screen, a cell for the detection of the X-rays that have crossed the object to be examined, placed being the image receiver, for converting a physical variable, characterizing the X-ray beam into a measurement signal L, an integrator circuit that integrates the measurement signal L for the duration S of the exposure to produce a signal M, and a device to compute the yield D given by the ratio of M to the product of the anode current I of the tube by the duration S of the exposure, wherein said method includes the following operations:

(a) a first calibration of the radiology system by means of objects with a thickness $E_p$ by using a receiver without the intensifier screen or screens so as to determine the yield $D_{se}$ from the function:

$$D_{se} = f(V_m, D_{se}) \quad (5)$$

(b) a second calibration of the radiology system by means of the objects with a thickness $E_p$ by using a receiver with an intensifier screen so as to determine the yield $D_c$ from the function:

$$D_c = f'(V_m, E_p) \quad (6)$$

the thickness $E_p$ from the inverse function:

$$E_p = g''(V_m, D_c) \qquad (7)$$

and compute the yield on the film $D_f$ function:

$$D_d = f'(V_m, E_p) - f''(V_m, E_p) \qquad (8)$$

(c) a third calibration to determine the reference lumination $L_{ref}$ that must be received by the film, under fixed reference conditions to achieve a blackening chosen as a reference value composing the following steps:
(e1) positioning the object to be radiographed;
(e2) triggering the start of the exposure;
(e3) estimating the mA·s remaining to be delivered and converting the mA·s into a signal in the united of the cell such that:

$$CE_{target} = mAs_{ra} \times D_c,$$

and, (e4) interrupting the exposure which consists in decrementing the target value $CE_{target}$ by the signals received by the cell and in terminating the exposure when the decremented value becomes smaller than or equal to a value $Val_o$.

31. A method according to claim 30, wherein the task of estimation (T.E.) is renewed periodically during the exposure at instants $t_1, t_2...t_n$ separated by a duration that is at least equal to the calculating time $t_c$.

32. A method for automatically determining the exposure time of a radiographic film in a system of radiology designed to examine an object that includes an X-ray tue, the supply voltage V which may assume various values $V_m$, with continuous or discrete variation, said X-ray tube emitting an X-ray beam in the form of pulses of variable duration S towards the object to be examined, an image receiver of the X-radiation that has crossed the object to form an image of said object, said receiver being constituted by at least one intensifier screen, a film sensitive to the light emitted by this screen, a cell for the detection of the X-rays that have crossed the object to be examined, placed behind the image receiver for conducting a physical variable, characterizing the X-ray beam, into a measurement signal L, an integrator circuit that integrates the measurement signal L for the duration S of the exposure to produce a signal M, and a device to compute the yield D given by the ratio of M to the product of the anode current I for the tube and the duration S of the exposure $I \times S(mA \cdot s)$, wherein said method includes the following operations:

(a) calibration of the radiological system so as to determine the analytical model $$D'_f = f'''(V_m, E_p)$$

with the film as the image receiver;

(b) a second calibration to determine the reference lumination $L_{ref}$ that must be received by the film, under fixed reference conditions, to achieve the blackening (or optical density) chosen as a reference value by the practitioner;

and then the following steps of:
(e1) positioning the object to be radiographed;
(e2) triggering the start of the exposure by the practitioner;
(e3) measuring the yield $D'_{f_1}$ at a certain time $t'$ after the start of the exposure;
(e4) calculating the lumination $L'_f$ received by the film by the equation:

$$L'_f = L_{am} + D'_{f_1} \times \delta mA \cdot s / CNRD \text{ (film dose rate)};$$

(e5) calculating the lumination $L'_{ra}$ remaining to be acquired to obtain the chosen blackening (or optical density) by the equation:

$$L'_{ra} = L_{ref} - L'_f$$

and (e6) calculating the estimated mA·s remaining to be delivered $mAs'_{ra}$ to obtain the blackening (or optical density) by the equation:

33. A method according to claim 32 the thickness $E_p$ is reduced by (sup.filter), the equivalent thickness due to the additional filtration resulting from the attenuation between the receiver film and the detection cell.

* * * * *

UNITED STATES PATENT AND TRADEMARK OFFICE
CERTIFICATE OF CORRECTION

PATENT NO. : 5,218,625
DATED : June 8, 1993
INVENTOR(S) : Robert Heidsieck It is certified that error appears in the above-identified patent and that said Letters Patent is hereby corrected as shown below:

Column 3, line 7, after "designed" delete ",";
Column 3, line 13, after "object" delete ",";
Column 3, line 17, after "object" delete ",";
Column 3, line 21, after "for" delete ",";
Column 3, line 22, change "M a device" to
--M. A device--;
Column 3, line 44, after "function" insert --:--;
Column 3, line 48, after "function" insert --:--;
Column 4, line 23, change "mAs$_{me}$s" to --mAs$_{mes}$--;
Column 4, line 29, change "t$_o$" to --t$_c$--;
Column 5, line 53, after "t$_o$" insert --and--;
Column 6, line 22, delete "r";
Column 7, line 45, after "function" insert
--of the exposure time t,--;
Column 8, line 24, after "precise" delete ",.";
Column 8, line 25, after "Time" change "s" to --S--;
Column 12, line 34, after "calculations" insert --.--;
Column 15, line 11, change "di" to
--d$_i$-- (both occurrences);
Column 15, line 22, change "[log l/d]" to
--[log l/d]$^2$--;
Column 15, line 68, after "Io" change "to" to --t$_o$--;
Column 17, line 13, change "Ech$_1$," (second occurrence)
to --Echq--;

UNITED STATES PATENT AND TRADEMARK OFFICE
CERTIFICATE OF CORRECTION

PATENT NO. : 5,218,625

DATED : June 8, 1993

INVENTOR(S) : Robert Heidsieck

It is certified that error appears in the above-identified patent and that said Letters Patent is hereby corrected as shown below:

Column 17, line 29 (equation 27), change "F" to --$\Gamma$--;
Column 18, line 26, change "(10)" to --(10')--;
Column 18, line 29, change "mAs$_{ra}$to" to --mAs$_{ra}$ to--;
Column 20, line 11, change "Lfreceived" to
    --L$_f$ received--;
Column 21, line 40, change "Lfreceived" to
    --L$_f$ received--;
Column 21, line 55, change "equationL" to --equation:--;
Column 22, line 19, change "determined" to --determine--;
Column 22, line 59, change "d$_1$" to --d$_j$--;
Column 22, line 66, change "give" to --given--;
Column 23, after line 65, insert
    --D$_{fo}$ = f'(V$_o$,E$_o$) - f''(V$_o$,E$_o$)    (8)
    calculating the luminance L$_{film}$ on the film
    by the formula:--;
Column 24, line 13 (after equation 25) insert
    --with K= 2/log$_{10}$(2)--;
Column 24, line 21, delete ", or 14";
Column 24, line 63, before "chosen" insert
    --(or optical density)--;
Column 25, line 13, change to read
    --L$_{ra}$ = L$_{ref}$ - L$_f$--;

UNITED STATES PATENT AND TRADEMARK OFFICE
CERTIFICATE OF CORRECTION

PATENT NO. : 5,218,625

DATED : June 8, 1993

INVENTOR(S) : Robert Heidsieck

It is certified that error appears in the above-identified patent and that said Letters Patent is hereby corrected as shown below:

```
Column 29, line 12, change "composing" to --comprising--;
```
Column 25, line 33, change "determined" to --determine--;
Column 25, line 68, after "steps of" insert
   --(or operations for)--;
Column 26, line 9, change "[log ½]²" to --[log 1/d]²--;
Column 26, line 38, change "the" to --a--;
Column 26, line 64, change the equation to read
   --$L_{cvn} = L_{ref} \, x \, \exp[CVN/\Gamma x P x \, \text{Log}(10)]$--;
Column 27, line 7, change "tue" to --tube--;
Column 27, line 36, change "tue" to --tube--;
Column 27, line 64, change "tue" to --tube--;
Column 28, line 14, delete "of";
Column 28, line 38, change "tue" to --tube--;
Column 28, line 42, delete "of" and insert
   --for detecting-- therefor;
Column 28, line 47, change "being" to --behind--;

UNITED STATES PATENT AND TRADEMARK OFFICE
CERTIFICATE OF CORRECTION

PATENT NO. : 5,218,625

DATED : June 8, 1993

INVENTOR(S) : Robert Heidsieck

It is certified that error appears in the above-identified patent and that said Letters Patent is hereby corrected as shown below:

Column 28, line 61, delete equation (5) and substitute
 --$D_{se} = f'(V_m, E_p)$ (4)
 and the thickness $E_p$ from the inverse function:
 $E_p = g'(V_m, D_{se})$ (5)--;
Column 29, line 7, change "$D_d$" to --$D_f$--;
Column 29, line 36, change "tue" to --tube--;
Column 29, line 40, delete "of" and insert
 --for detecting-- therefor;
Column 30, line 39, after "equation:" insert
 --$mAs'_{ra} = L'_{ra}/D'_{fl} \times CNRD$ (film dose rate).--.

Signed and Sealed this

Seventeenth Day of May, 1994

BRUCE LEHMAN

*Commissioner of Patents and Trademarks*

*Attest:*

*Attesting Officer*